United States Patent [19]

Credle, Jr.

[11] 4,355,653
[45] Oct. 26, 1982

[54] VENTED CHECK VALVE

[75] Inventor: William S. Credle, Jr., Stone Mountain, Ga.

[73] Assignee: The Coca-Cola Company, Atlanta, Ga.

[21] Appl. No.: 263,093

[22] Filed: May 12, 1981

[51] Int. Cl.³ .............................................. G05D 7/00
[52] U.S. Cl. .................................. 137/102; 137/854; 261/DIG. 7; 251/61.1
[58] Field of Search ................. 251/61.1; 261/DIG. 7; 137/102, 854

[56] References Cited

U.S. PATENT DOCUMENTS

| | | | |
|---|---|---|---|
| 1,412,473 | 4/1922 | Lane | 137/102 |
| 1,506,012 | 8/1924 | Lewis | 137/102 |
| 2,567,391 | 9/1951 | Mead | 137/102 |
| 3,297,048 | 1/1967 | Imhof | 137/854 |
| 3,428,071 | 2/1969 | Köbnick | 137/102 |
| 3,465,786 | 9/1969 | Spisak | 251/61.1 |
| 3,599,657 | 8/1971 | Maldavs | 261/DIG. 7 |
| 3,636,968 | 1/1972 | Tine | 137/102 |
| 3,765,318 | 10/1973 | Mazza | 261/DIG. 7 |
| 3,780,198 | 12/1973 | Pahl et al. | 261/DIG. 7 |
| 4,084,606 | 4/1978 | Mittleman | 137/102 |

FOREIGN PATENT DOCUMENTS

| | | | |
|---|---|---|---|
| 2711387 | 9/1978 | Fed. Rep. of Germany | 137/854 |
| 1100192 | 9/1955 | France | 137/102 |
| 2062116 | 7/1978 | France | 137/102 |

Primary Examiner—H. Jay Spiegel
Attorney, Agent, or Firm—Birch, Stewart, Kolasch & Birch

[57] ABSTRACT

The present invention describes a vented check valve for use with post-mix carbonators. The vented check valve is a fail safe device which will vent carbon dioxide or carbonated water to the atmosphere when a back flow condition occurs. The vented check valve of the present invention includes a flexible valve diaphragm having a first valve seat portion around the annular portion of the diaphragm and a second valve seat portion in the center thereof. The first valve seat portion is utilized to open and close the main water inlet by permitting the edges of the diaphragm to flex in response to the pressure of water flowing in a first direction. The second valve seat portion is disposed in cooperation with a vent passage and seats firmly on the vent passage while water flows in the first direction, but unseats from the vent passage permitting the water to flow out of the valve, through the vent passage to the atmosphere when a back flow condition occurs, i.e., namely, when the water flows in a direction opposite to the first direction.

4 Claims, 7 Drawing Figures

4,355,653

VENTED CHECK VALVE

BACKGROUND OF THE INVENTION

1. Field of the Invention

The present invention generally relates to vented check valves for use with post-mix carbonators for preventing carbon dioxide or carbonated water from entering a water supply system.

2. Description of the Prior Art

The vented check valve of the present invention solves problems in post-mix carbonators with respect to the backflow of carbon dioxide or carbonated water into copper pipes of the water supply system. The carbonated water causes leaching of copper out of these pipes. This copper can cause immediate vomiting and sickness when taken in excessive amounts. A majority of the carbonators in use today use double check valves to prevent the backflow of carbonated water into water systems. Recently, however, several states have passed regulations stating that existing carbonators must be retrofitted with vented check valves. These vented check valves are failsafe devices that vent carbon dioxide or carbonated water to the atmosphere if a malfunction occurs in the double check valves.

Testing of the currently available vented check valves of the prior art has yielded results which indicate that these conventional vented check valves are prone to failure and many of them last less than two years in the field. In addition, the prior art vented check valves are unnecessarily complex due to the number of moving parts inside the valve. One example of such a complex prior art valve is illustrated in U.S. Pat. No. 3,636,968 to Tine. In this valve, a shaft 57 is used to support a valve structure including a multiplicity of parts 58c, 60, 66, 64, 70, 68, 66A, 74, 57A, 57C, 57D, 60A, 60B and 52.

THE SUMMARY OF THE INVENTION

It is a primary object of the present invention to provide a vented check valve which exhibits an increased simplicity and hence reliability over the vented check valve of the prior art.

Another object of the present invention is to provide a vented check valve which has fewer parts, and is less expensive, than the vented check valves of the prior art.

A still further object of the present invention is to provide a vented check valve which has essentially only one moving part.

Still another object of the present invention is to provide a vented check valve having a flexible elastomeric diaphragm which includes a neck portion which seats firmly in a vent passage when no back flow condition occurs, but which unseats from the vent passage when a back flow condition occurs, thereby venting the unwanted carbon dioxide or carbonated water to the atmosphere.

Still another object of the present invention is to provide a vented check valve which is more sanitary, and is free of crevises and dead-spots found in the conventional vented check valves of the prior art.

A still further object of the present invention is to provide a check valve having a simpler configuration than the configuration of the prior art vented check valves.

These and other objects of the present invention are accomplished by designing the vented check valve to include a flexible valve diaphram having a first valve seat portion around an annular portion thereof and a second valve seat portion in the center thereof. The first valve seat portion is utilized to open and close the main water inlet by permitting the edges of the diaphram to flex in response to the pressure of water flow in a first direction. The second valve seat portion is a plug-shaped portion extending outwardly from the center of the flexible valve diaphragm and formed integrally therewith. The plug-shaped portion is disposed to cooperate with a vent passage. The first and second valve seat portions are disposed in a chamber internally of said vented check valve. The plug-shaped portion seats on one end of the vent passage while fluid flows in a first direction but unseats from the one end of the vent passage permitting fluid ($CO_2$, gas, soda, etc.) to flow out of the valve to the atmosphere when a backflow condition occurs, i.e., namely, when fluid flows in a direction opposite to the first direction. The one end of the vent passage defines an opening having sloped sidewalls converging from the walls of the chamber toward the tip portion of the vent passage. The diameter of the opening, at the one end of the vent passage is larger than the diameter of the top of the plug-shaped portion enabling the plug-shaped portion to self-center in the opening. As a result, the diaphragm is supported in the chambers, in the absence of fluid flow, solely by the self-biasing force of the flexible diaphragm between the first and second valve seats.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention and wherein.

DESCRIPTION OF THE PREFERRED EMBODIMENT

Figure 1:
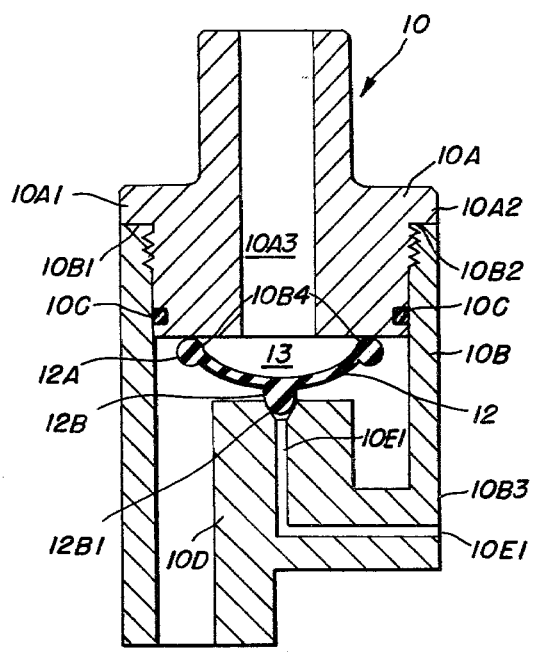
FIG. 1 is a cross-sectional view of a first embodiment of the vented check valve of the present invention.

Referring to FIG. 1, a cross-sectional view of the vented check valve 10 of the present invention is illustrated. The body of the vented check valve 10 includes a male portion 10A and a female portion 10B. The male portion includes two outer peripheral flanges 10A1 and 10A2 which are designed to abut against the upper surfaces 10B1 and 10B2 of the female portion 10B when the male portion 10A is screwed into the female portion 10B. A sealing means 10C is disposed between the internal surface of the female portion 10B and the external annular surface of the male portion 10A. When water or other fluid flows through the vented check valve, the sealing means 10C seal the internal surface of the female portion 10B to the external annular surface of the male portion 10A, to preclude leaks therebetween.

One side of the lower end 10B3 of the female portion 10B is integral with a vent pipe 10D. This vent pipe extends longitudinally of the female portion, and terminates at a point which is very close to one end of the male portion 10A. This vent pipe has a vent passage 10E extending axially through the center thereof. The vent passage 10E extends from the external annular surface of the female portion 10B through the center of vent pipe 10D and terminates internally of the female portion 10B at a point in close proximity to one end of the male portion 10A. Thus, the contents of the vented check valve, internally of the female portion 10B communicate with the atmosphere by way of the vent passage 10E.

The outer dimension or diameter of vent pipe 10D is less than the inner dimension of female portion 10B, thereby forming an annular space therebetween. When fluid flows through the vented check valve in the first direction (during normal operation), it will pass through the annular space between the female portion 10B and the vent pipe 10D.

The vented check valve 10 of the present invention also includes a resilient flexible diaphragm 12 comprised of an elastomer, plastic, or other similar material. The flexible diaphragm is normally unflexed, and the outer peripheral edges of the major portion of the diaphragm are pointed upward such that the outer annular ring 12A of the major portion of the flexible diaphragm 12 is in contact with the lower surface 10A3 of the male portion 10A forming a first valve seat. The flexible diaphragm 12 also includes a plug-shaped portion 12B which is disposed at the center of the flexible diaphragm 12. The plug-shaped portion 12B is formed integrally with the major portion of the flexible diaphragm 12 and is made of the same elastomer or plastic-like resilient material as is the major portion of the flexible diaphragm. The plug-shaped portion 12B extends outwardly from the flexible diaphragm 12, along an axis which passes perpendicularly through the center of the flexible diaphragm 12. A tip portion 12B1 of the plug-shaped portion 12B is adapted to seat firmly within vent passage port 10E1 during normal operation of the vented check valve of the present invention forming a second valve seat. Normal operation is defined as that operation wherein a backflow condition of carbonated water has not occurred. The vent passage port 10E1 forms a vent seat wherein the tip portion 12B1 of the plug-shaped portion of 12B fits firmly within the vent seat during normal operation of the vented check valve 10 of the present invention. An expanded view of the vent passage port 10E1 in close proximity to the one end of the male portion 10A can be seen in FIG. 6A. The vent passage port 10E1 defines an opening 10E11 having sloping sidewalls 10E12 which converge from the walls 10E13 of the chamber, occupied by the flexible diaphragm 12, toward the tip 10E14 of the vent passage port 10E1. The opening 10E11 is larger in its outer dimension (eg—diameter) than the outer dimension (diameter) of the tip 12B1 of the plug-shaped portion 12B. Since the outer dimension of the opening is larger, the plug-shaped portion 12B will self-center in the opening 10E11. In addition, referring to FIG. 6B, in the absence of fluid flow, the dimension A, the difference between the diameter of the opening 10E11 and the diameter of the tip 12B1 of plug 12B, and the dimension B, the difference between the dimension of the chamber in the plane of the major dimension of the diaphragm and the major dimension of the diaphragm are related such that the plug helps to center the diaphragm and the diaphragm outer periphery helps center the plug.

Figure 6A:
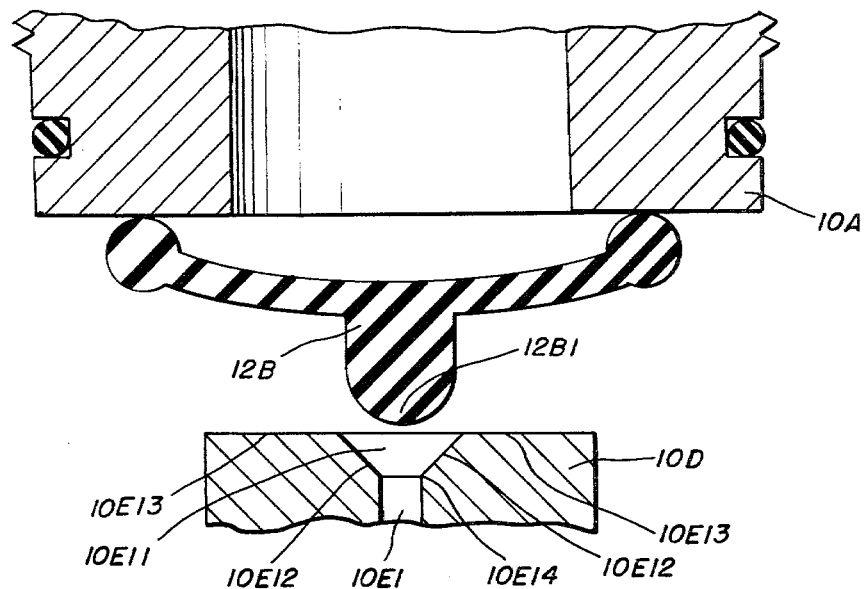
FIGS. 6A and 6B are enlarged views of a portion of the vented check valve of the present invention illustrating the operation thereof.
Figure 6B:
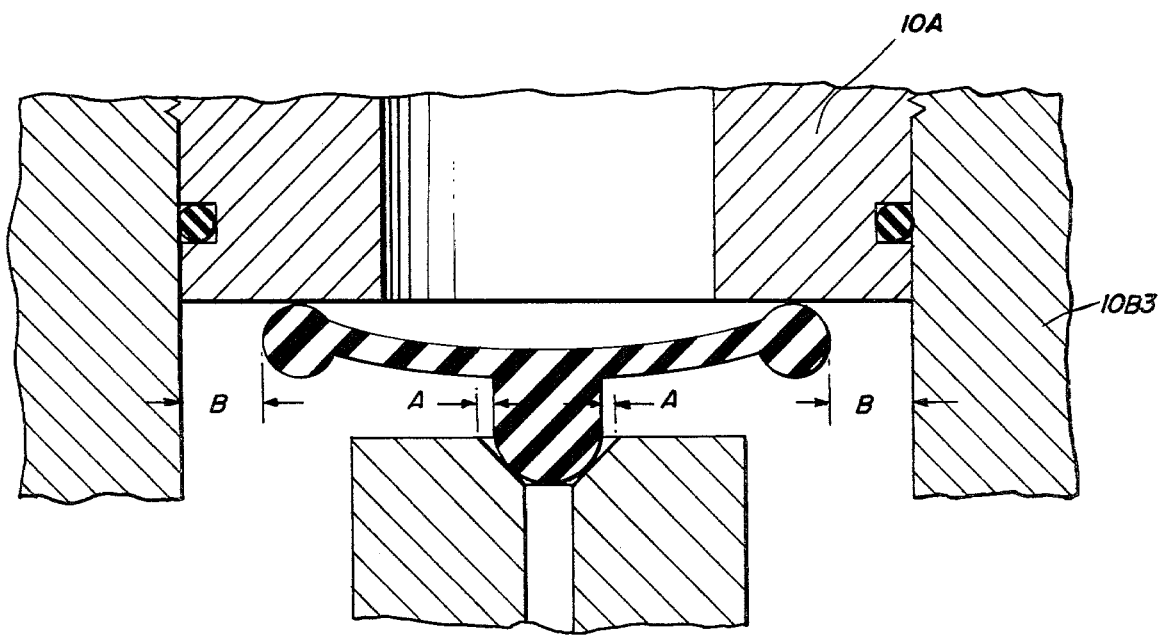

Referring back to FIG. 1, the diaphragm 12 resides in a chamber 13 defined as the space formed between the one end of the male portion 10A (surface 10A3 of male portion 10A) and the one end of the conduit 10D (surface 10E13 as shown in FIG. 6A). The diaphragm 12 is supported in the chamber 13, in the absence of fluid flow, solely by the self-biasing force of the flexible diaphragm 12 between the first and second valve seats. Furthermore, the male portion 10A and the female portion 10B, when assembled, compress the flexible diaphragm 12 between the first and second valve seats in the absence of fluid flow through the vented check valve 10.

Figure 5:
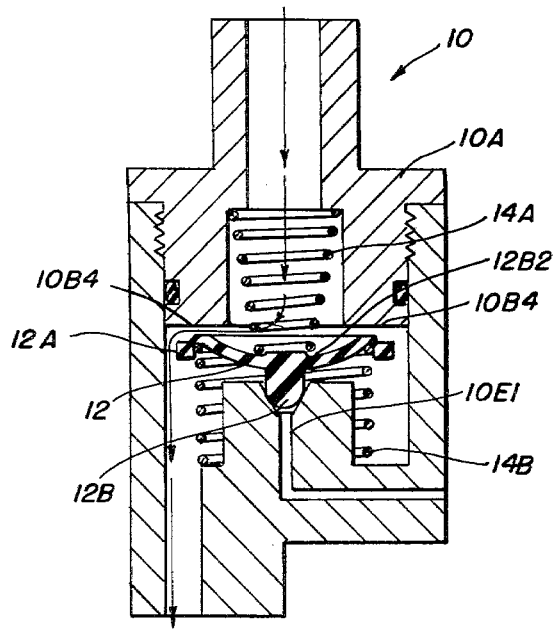
FIG. 5 represents the vented check valve of the present invention taken in cross-section, and further including a plurality of springs for holding the outer peripheral portion of the flexible diaphragm in a sealed position and also holding the neck portion of the flexible diaphragm tightly against the vent passage for proper performance of the check valve.

Referring to FIG. 5, a further embodiment of the vented check valve 10 of the present invention is shown. This embodiment is not a preferred embodiment, since one of the major objects of this invention is the elimination of unnecessary parts. However, this embodiment is preferred over the prior art since fewer moving parts are used in the FIG. 5 embodiment relative to the prior art. In FIG. 5, a plurality of springs are utilized for maintaining a proper seal of the flexible diaphragm 12 in its proper position within the vented check valve 10 of the present invention. For example, spring 14A is in contact with the upper central surface 12B2 of the flexible diaphram 12 and normally biases the flexible diaphram 12 from above, such that the tip portion 12B1 of the neck portion 12B seats firmly within the vent portion port 10E1.

Spring 14B biases the annular peripheral portion 12A of the flexible diaphram 12, from below maintaining this peripheral portion 12A in contact with the lower surface area 10B4 of the male portion 10A.

Figure 2:
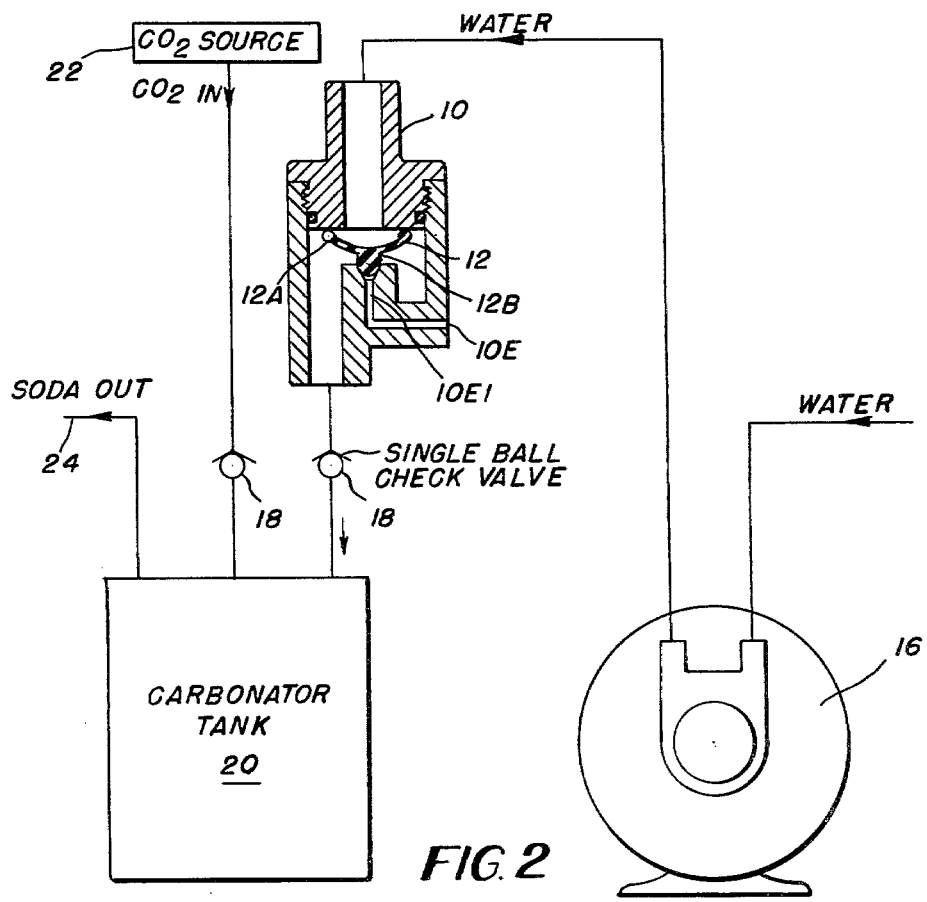
FIG. 2 is a diagram of the vented check valve of the present invention used in conjunction with a check valve(s) on a standard post-mix carbonator.

Referring to FIG. 2, the vented check valve 10 of the present invention is shown in a system which includes a check valve(s) on a standard post-mix carbonator. Still water enters a pump 16 through the standard pipe line, and exits the pump 16 for entry into the vented check valve 10 of the present invention. A check valve(s) 18 may be used to prevent the carbon dioxide or carbonated water from a carbonator tank from entering the vented check valve 10 and thus preventing a back flow condition from taking place, namely, preventing the $CO_2$ or carbonated water from flowing upward and into the vented check valve 10 of the present invention. In the event that the check valve fails, the vented check valve vents fluid to atmosphere while sealing off the inlet fluid line. The carbonator tank 20 mixes the still water coming from the vented check valve 10 and the carbon dioxide which is entering the carbonator tank from the external carbon dioxide source 22. The resultant soda water exits the carbonator tank 20 at the exit port 24.

Figure 3:
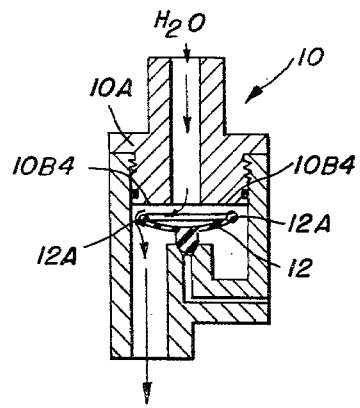
FIG. 3 represents a cross-sectional view of the vented check valve of the present invention illustrating the manner by which the flexible diaphragm will permit fluid to flow therethrough during normal operation of the device.

In operation, referring to FIG. 3, still water enters the vented check valve 10 from the top portion thereof from pump as shown in FIG. 3. The pressure of the water will force the annular peripheral portion 12A of the flexible diaphragm 12 to flex downwardly such that it will unseat from the lower portion 10B4 of the male portion 10A. Thus, the water will flow normally through the vented check valve of the present invention, as shown in FIG. 3. This downward water pressure also helps to seal the vent orifice. A backflow condition of carbonated water has not yet occurred during the normal operation of the device. Since the outer walls 10E12 of the opening 10E11 are sloping, converging to the tip 10E14 of the vent passage port, and since the diameter of the opening 10E11 is larger than the diameter of the plug 12B, the plug-shaped portion 12B will be self-centering and essentially self-sealing in the opening 10E11 during normal operation.

Figure 4:
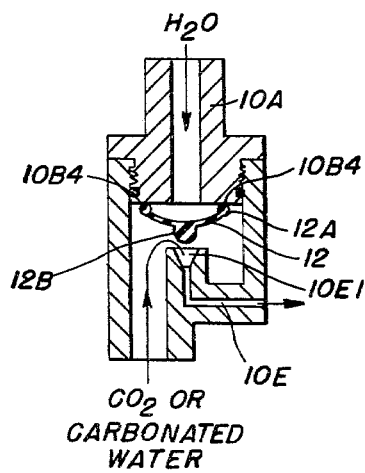
FIG. 4 represents the vented check valve of the present invention during a backflow condition illustrating the manner by which the flexible diaphragm, in particular, the neck portion, will unseat from the vent passage allowing the carbonated water or carbon dioxide to vent to the atmosphere through the vent orifice while sealing off the inlet water line.

However, as shown in FIG. 4, if the downstream check valve fails and a backflow condition is created, $CO_2$ or carbonated water will flow upwardly from carbonator tank 20 into the vented check valve. The pressure of the $CO_2$ or carbonated water flowing upwardly into the vented check valve 10 will force the outer peripheral portion 12A of the flexible diaphragm 12 to seat on the lower portion 10B4 of the male 10A. In addition, the pressure of the $CO_2$ or carbonated water will cause the plug-shaped portion 12B of the flexible diaphram 12 to unseat from the vent seat or vent passage port 10E1. Thus, a passageway will be created through the vent passage 10E, permitting the $CO_2$ or carbonated water to vent to the atmosphere and not contaminate the water supply.

As shown in FIG. 2, as the water enters the vented check valve 10 from the pump 16, the outer peripheral portion 12A of the flexible diaphragm 12 will flex downwardly thereby permitting the water to flow through the vented check valve 10, through the downstream check valve(s) (18), and into the carbonator tank 20. $CO_2$ will enter the carbonator tank 20 from the $CO_2$ source 22, passing through the check valve(s) 18 on its way to the carbonator tank 20. If the single ball check valve 18 malfunctions, a backflow condition will be created within the vented check valve 10 of the present invention. In this case, $CO_2$ or carbonated water will travel upward through the check valve(s) 18 and into the vented check valve 10.

As a result, the pressure of the $CO_2$ or carbonated water will force the central portion of the flexible diaphram 12 to flex upwardly thereby unseating the neck portion 12B of the flexible diaphragm 12 from the vent seat or vent passage port 10E1. When the neck portion 12B unseats from the vent passage port 10E1, the $CO_2$ or carbonated water, entering the vented check valve 10 from the carbonator tank 20, will vent to the atmosphere through the vent passage 10E. In this way, during a backflow condition, the $CO_2$ or carbonated water will not enter the water pipe line and will therefore not leach the copper out of the water pipe line.

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

I claim:

1. In a post-mix beverage carbonator system including a water supply, a source of carbon dioxide gas, a carbonator tank for mixing the water from the water supply with the carbon dioxide gas and producing a carbonated water mixture, supply pipes for connecting said carbonator tank to said water supply, pumping means for pumping the water from the water supply to the carbonator tank, and check valve means disposed between said carbonator tank and said pumping means, the improvement comprising:

vented check valve means disposed between said check valve means and said pumping means for passing said water therethrough in one direction during normal operation and preventing the carbonated water mixture in the carbonator tank from backflowing into said supply pipes in an opposite direction in the event of a malfunction in the operation of said check valve means, said vented check valve means including a body portion having a chamber therein containing a movable valve element, an inlet passage and two outlet passages communicating with said chamber, a first of said outlet passages having a first opening on an opposite side of said chamber from said inlet passage and aligned therewith and a second opening communicating with the atmosphere, the walls of said chamber surrounding said inlet passage defining a first valve seat, said first opening of said first outlet passage defining a second valve seat, a second outlet passage communicating with said chamber in a position offset from said inlet and said first outlet passages, said movable valve element connecting only said inlet passage and said second outlet passage though said chamber during said normal operation and connecting only said first and second outlet passages through said chamber during said backflow condition, an improvement in said movable valve element comprising:

a flexible diaphragm having an annular sealing portion for operative engagement with said first valve seat and a plug-shaped sealing portion extending therefrom and integral therewith for operative engagement with said second valve seat;

said flexible diaphragm in the absence of fluid flow through said valve body being self-biased in a first shape so that said annular sealing portion firmly seats on said first valve seat and said plug-shaped portion firmly seats in said opening defining said second valve seat;

said flexible diaphragm during said normal operation having a second shape wherein said annular sealing portion is unseated from said first valve seat and said plug-shaped portion is firmly seated in said second valve seat;

said flexible diaphragm during said backflow condition having a third shape wherein said annular sealing portion firmly seats on said first valve seat and said plug-shaped portion is unseated from said second valve seat; and wherein said opening defining said second seat has sloped side walls converging from the walls of said chamber toward said first outlet passage, said opening at the walls of said chamber being larger than the diameter of the tip of said plug-shaped portion, whereby said plug-shaped portion self-centers in said opening.

2. The invention of claim 1 wherein said flexible diaphragm is supported in said chamber in the absence of fluid flow solely by the self-biasing force of said flexible diaphragm between said first and second valve seats.

3. The invention of claim 2 wherein said valve body comprises a first separable body portion including said first valve seat and a second separable body portion including said second valve seat, said first and second body portions when assembled compressing said flexible diaphragm between said first and second valve seats in the absence of fluid flow through said valve body.

4. The invention of claim 1 further comprising:
first spring means for further biasing said plug-shaped portion into seated engagement with said second valve seat; and
second spring means for further biasing said annular sealing portion into engagement with said first valve seat.

* * * * *